United States Patent [19]
Bucci et al.

[11] Patent Number: 5,998,361
[45] Date of Patent: Dec. 7, 1999

[54] POLYMERIZED HEMOGLOBIN

[75] Inventors: Enrico Bucci, Timonium; Anna Razynska, Catonsville, both of Md.

[73] Assignee: University of Maryland at Baltimore, Baltimore, Md.

[21] Appl. No.: 08/733,413

[22] Filed: Oct. 18, 1996

[51] Int. Cl.⁶ ..................................................... A61K 35/14
[52] U.S. Cl. .................. 514/2; 514/6; 530/380; 530/385
[58] Field of Search ..................... 530/385, 380; 514/6, 2

[56] References Cited

U.S. PATENT DOCUMENTS

| | | | |
|---|---|---|---|
| 5,349,054 | 9/1994 | Bonaventura et al. | 530/385 |
| 5,387,672 | 2/1995 | Bucci et al. | 530/385 |
| 5,753,616 | 5/1998 | Rausch et al. | 514/6 |

OTHER PUBLICATIONS

Grabarek et al, *Analytical Biochemistry,* 185:131–135 (1990).
Staros et al., "Enhancement of Water–Soluble Carbodiimide–Mediated Coupling Reactions" Anal. Biochem., v. 156, pp. 220–222, 1986.
Acharya et al., "Reactivity of Glu–22(β) of Hemoglobin–S for Amidation with Glucosamine" Biochemistry, v. 24, p. 4885–4890, 1985.
Grabarek, "Zero Length Crosslinking Procedure w/Use of Active Esters" Anal. Biochem., v. 185, pp. 131–135, 1990.

*Primary Examiner*—Johann Richter
*Assistant Examiner*—Patrick R. Delaney
*Attorney, Agent, or Firm*—Sughrue, Mion, Zinn, Macpeak & Seas, PLLC

[57] ABSTRACT

Stroma-free hemoglobin intermolecularly cross-linked, i.e., polymerized, so as to transform stroma-free hemoglobin into a physiologically competent oxygen carrier which is retained in vivo for adequate periods of time, and thus can be used in fluids for transporting oxygen is described.

45 Claims, 4 Drawing Sheets

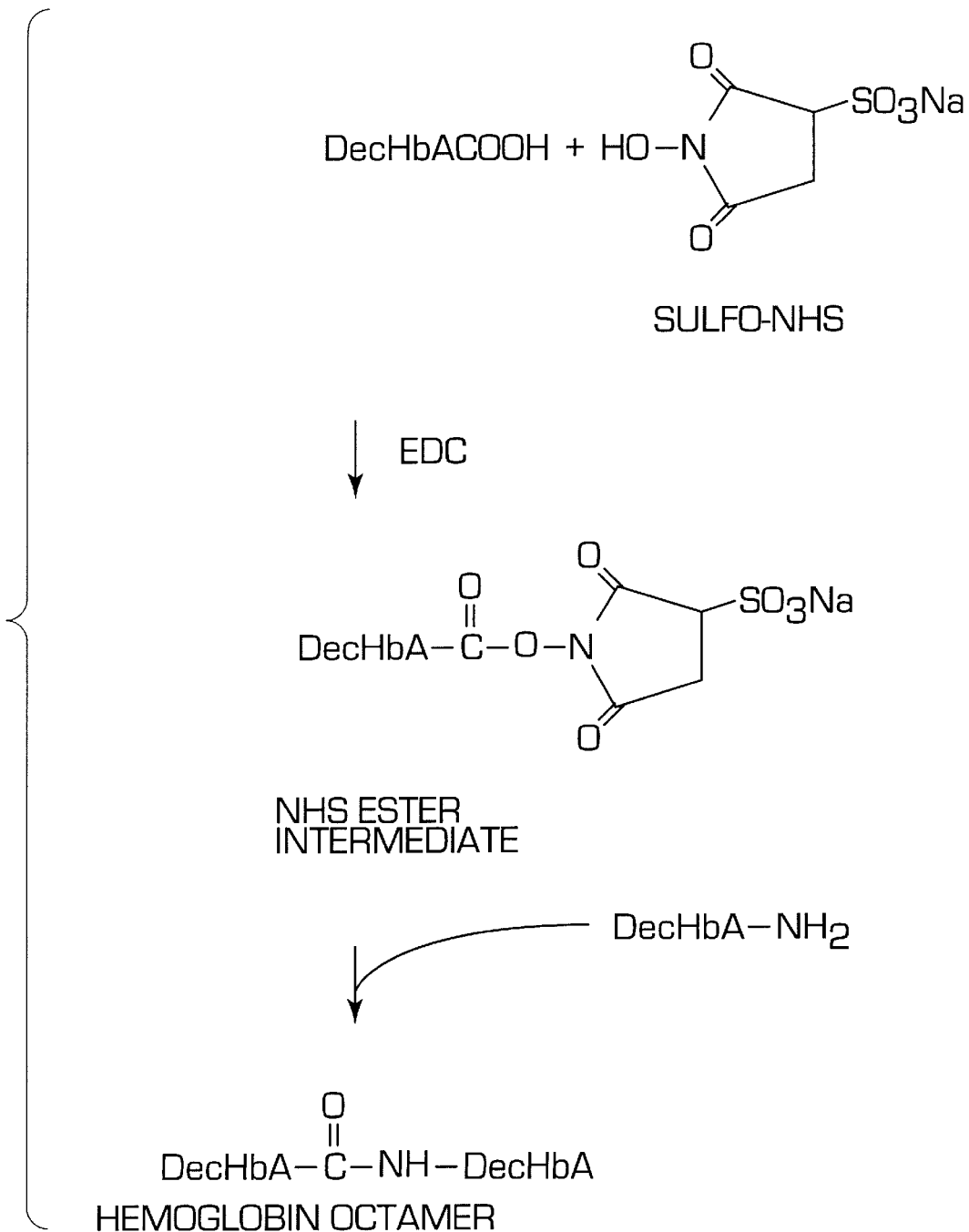

POLYMERIZED HEMOGLOBIN

The development of the present invention was supported by the University of Maryland and NIH grant Nos. RO1-Hl-13164 and PO1-HL-48517.

FIELD OF THE INVENTION

The present invention relates to hemoglobin which has been polymerized such that it is useful as a physiologically competent oxygen carrier. As defined herein, "physiologically competent" or "physiologically acceptable" with respect to the oxygen carrier means that the oxygen carrier can absorb oxygen at the partial pressures of oxygen prevailing at the site of oxygenation of hemoglobin, e.g., in the lungs of humans or other air-breathing organisms and in the gills of fish, and release it to the tissues of the same organisms in amounts which are life supporting, at least when the organisms are in a resting state.

BACKGROUND OF THE INVENTION
1. Stroma-Free Hemoglobin

Hemoglobin solutions have long been proposed as cell-free oxygen carriers to be used as red cell substitutes in infusional fluids. The interest in these compounds stems from their potential clinical applications. They can be sterilized, easily stored, and used in transfusions without blood-group typing.

Intravenously injected (infused) crude hemolysates and extensive hemolytic processes produced in vivo by immunological reactions involving intravascular lysis of red blood cells, are known to produce a clinical syndrome characterized by disseminate intravascular coagulation. This syndrome is often fatal and is produced by the residual red blood cell walls (stroma) and their fragments, so infused into circulating blood. Stroma-free hemolysates do not show this toxicity (See Rabiner et al, *J. Exp. Med.,* 126:1127 (1967)). As a result, it has been desired to use stroma-free hemoglobin as an oxygen carrier in cell-free transfusional fluids.

However, the use of stroma-free hemoglobin has the following two disadvantages: In vivo, the retention time of the stroma-free human hemoglobin is very short, i.e., it has a half-life on the order of 1–4 hr (see Rabiner et al, supra; and De Venuto et al, *Transfusion,* 17:555 (1977)). "Half-life" is defined as the time necessary to eliminate 50% of the infused hemoglobin from circulating blood. Further, outside of the red blood cells, hemoglobin has a high affinity for oxygen which, in vivo, would prevent the release, i.e., the transport, of oxygen from hemoglobin to the tissues. These disadvantages are directly the result of the molecular structure of hemoglobin.

Hemoglobin is a tetrameric molecule having a molecular weight of 64,500 Daltons. The tetrameric molecule is formed of two pairs of $\alpha$ and $\beta$ subunits. The subunits are held together as a result of ionic, hydrophobic and Van der Waals forces, and not as a result of covalent bonds. When hemoglobin is oxygenated, i.e., combined with oxygen, it readily forms $\alpha$-$\beta$ dimers having a molecular weight of 32,250 Daltons. These dimers are not retained in vivo by the kidneys and are eliminated through the urine. In the rat, untreated hemoglobins are rapidly eliminated in the urine and have a half retention time of only 40–50 min. Urine elimination is the result of the dissociation of tetrameric hemoglobins into dimers.

The tetrameric structure of hemoglobin also provides a binding site for 2,3-diphosphoglycerate. Inside red blood cells, 2,3-diphosphoglycerate combines with hemoglobin in order to decrease its oxygen affinity to a level compatible with oxygen transport. The binding of 2,3-diphosphoglycerate and hemoglobin is purely electrostatic and no stable covalent bonds are formed. Thus, when red blood cells are ruptured and 2,3-diphosphoglycerate is not retained inside the cells by the cell wall, it is released from hemoglobin. As a result, hemoglobin acquires a higher oxygen affinity. This prevents the transport of oxygen from hemoglobin to the tissues. The level of this higher affinity is sufficient such that the oxygen affinity can be considered "non-physiological".

Because of the many appealing qualities of hemoglobin, i.e., its ability to reversibly bind oxygen, the low viscosity of a hemoglobin solution and its easy preparation and storage for long periods of time, various attempts have been made in order to overcome the above described disadvantageous characteristics of stroma-free hemoglobin. These various attempts are discussed in more detail below.

2. Chemical Treatments for Preventing the Formation of Dimers

The formation of $\alpha$-$\beta$ dimers, which are not retained in vivo, can be prevented by coupling the tetrameric molecules of hemoglobin with large molecular weight matrices, ranging from 20,000 to 275,000 Daltons. For example, matrices such as dextran (see Tam et al, Can. *J. Biochem.,* 56:981 (1978); and Bonneaux et al, *Experientia,* 37:884 (1981)) and hydroxyethyl starch (see Baldwin et al, *Tetrahedron,* 3:1723 (1981); and U.S. Pat. Nos. 4,412,989, 4,900,816, 4,650,786 and 4,710,488) have been employed. This coupling prevents the elimination of hemoglobin in vivo from the kidneys by way of the urine. Other types of polymeric coupling employing collagen, collagen degradation products, and gelatin as a supporting matrix have also been employed (see U.S. Pat. No. 2,591,133; U.S. Pat. No. 3,057,782; and Bowes et al, *Biochem. Biophys. Acta.,* 168:341 (1968)). However, the oxygen affinity of the resulting coupled hemoglobin is even higher than that of stroma-free hemoglobin, and thus hemoglobin coupled in this manner cannot be advantageously employed as an oxygen transport medium.

Other known treatments for preventing the formation of $\alpha$-$\beta$ dimers are based on reactions which polymerize the tetrameric molecules of hemoglobin to form so-called "polyhemoglobins". Polyhemoglobins can be obtained using bifunctional reagents, such as glutaraldehyde (see Hopwood et al, *Histochem. J.,* 2:137 (1970)) or diimidate esters (see Mock et al, Fed. Proc., 34:1458 (1975); and U.S. Pat. No. 3,925,344). These bifunctional reagents form covalent bonds between the amino groups present on the surface of different hemoglobin molecules producing intermolecular cross-links. There are 40 or more of such amino groups belonging to lysyl residues on the surface of mammalian hemoglobins (44 in human hemoglobin). Thus, a large number of possible combinations of hemoglobin molecules occur. As a result, the polyhemoglobin reaction products are a heterogeneous mixture of various molecular species which differ in size and shape. The molecular weights thereof range from 64,500 to 600,000 Daltons. Longer retention times in vivo are obtained using polyhemoglobins.

Besides the various treatments discussed above which result in formation of heterogeneous mixtures of polyhemoglobin, reagents have been developed which are capable of producing an internal cross-link of the hemoglobin subunits with little or no formation of polyhemoglobins. More specifically, the formation of cross-links between the $\beta$ subunits of hemoglobin using 2-N-2-formylpyridoxal-5'-phosphate and borohydride and bis-pyridoxal polyphosphates have been carried out (see Benesch et al, *Biochem. Biophys. Res. Comm.,* 62:1123 (1975); and Benesch et al, Biochem. *Biophys. Res. Comm.,* 156:9 (1988)). The oxygen affinity of the. thus treated hemoglobin is decreased to levels similar to that of normal blood. However, the reagents employed therein are very difficult and costly to synthesize, and thus these methods are disadvantageous.

Other reagents have been employed in order to effect internal cross-linking of the hemoglobin subunits. These reagents are commonly known as "diaspirins". Diaspirins are diesters of 3,5-dibromosalicyl containing succinyl, fumaryl or other dicarboxylic acid residues. These reagents produce covalent cross-links between two $\beta$ or two $\alpha$ subunits of an individual hemoglobin molecule. While better results are obtained using liganded (oxy- or carboxy-) hemoglobin, such a treatment does not sufficiently affect the oxygen affinity characteristics of stroma-free hemoglobin, and thus can not be advantageously employed (see Walder et al, *J. Mol. Biol.,* 141:195 (1980); and U.S. Pat. Nos. 4,061, 736, 4,001,200, 4,001,401, and 4,053,590).

It should be stressed that according to pertinent literature, i.e., Walder, *Biochem.,* 18:4265–4270 (1779); Walder et al, *J. Mol. Biol.,* 141:195 (1980); and Zaugg, *J. Biol. Chem.,* 255:2816–2821 (1980), activated dicarboxylic acid of increasing length, above that of the 4-carbon chain of succinic and fumaric acid, show a progressively lower reactivity with both liganded and unliganded hemoglobin so that activated sebacic acid (10-carbons long) produces no reactions with human hemoglobin.

In U.S. Pat. Nos. 4,473,496 and 4,857,636, linear $\alpha$-$\omega$ or heterocyclic polyaldehydes containing negatively charged groups are described as suitable for both decreasing the oxygen affinity of hemoglobin and for producing inter- and intramolecular cross-linking of hemoglobin. These reagents include carbohydrate-containing molecules, such as raffinose, and mono- and polyphosphorylated nucleotides partially oxidized with periodate, so as to obtain aldehydic groups. The coupling reaction is based on the formation of Shiff bases of the aldehydic groups with the amino groups of the hemoglobin molecule. The Shiff bases are then transformed into covalent bonds by reduction with sodium or potassium borohydride, or another strong reducing agent.

In U.S. Pat. No. 4,584,130, cross-linking of hemoglobin with bifunctional reagents is disclosed. The reagents disclosed therein are based on an electron withdrawing group which modulates the reactivity of two peripheral active groups. However, the electron withdrawing group remains within the cross-linking bridge after the reaction. In the reagent of the present application, when an electron withdrawing group is employed, it is present in the leaving group only (e.g., 3,5-dibromosalicyl), and therefore it does not remain in the cross-linking bridge after the chemical reaction of the activated carboxyls with the amino groups of the protein.

3. Chemical Treatments for Decreasing the Oxygen Affinity of Stroma-Free Hemoglobin The most widely used chemical modification of stroma-free hemoglobin so as to decrease the oxygen affinity thereof employs the use of pyridoxal-5'-phosphate and sodium or potassium borohydride (see Bensch et al, *Biochem.,* 11:3576 (1972)). The resulting product is commonly referred to as "PLP-hemoglobin" and has satisfactory oxygen affinity, i.e., oxygen affinity very near that of the red cells present in normal blood.

Other known chemical modifications of hemoglobin have been carried out using phosphoric acid derivatives of carbohydrates (e.g., glucose-6-phosphate) (see McDonald et al, *J. Biol. Chem.,* 254:702 (1979)); carbamylation (see Manning, *Meth. Enz.,* 76:159 (1981)) and carboxymethylation (see DiDonato et al, *J. Biol. Chem.,* 258:11890 (1983)). In each of these treatments, the amino-terminal end of the $\beta$ subunit of hemoglobin is permanently substituted with the above described reagents.

In addition, none of these chemical treatments discussed in this section stabilize the tetrameric structure of hemoglobin so as to prevent the formation of $\alpha$-$\beta$ dimers. Thus, the resulting hemoglobins do not have prolonged retention times in vivo.

4. Combined Chemical Treatments for Preventing the Formation of $\alpha$-$\beta$ Dimers and Decreasing the Oxygen Affinity of Stroma-Free Hemoglobin As discussed above, the production of physiologically competent stroma-free hemoglobin-based oxygen carriers necessitates two separate treatments. That is, one treatment is necessary for preventing the formation of $\alpha$-$\beta$ dimers in vivo and a second treatment is required for decreasing its oxygen affinity. The most widely employed combination of treatments is that of reacting glutaraldehyde with PLP-hemoglobin to form pyridoxylated polyhemoglobins (see Seghal et al, *J. Surg. Res.,* 30:14 (1981)). Intramolecular cross-linking of PLP-hemoglobin has also been obtained using diaspirins (see Tye et al, *Prog. Clin. Biol. Res.,* 22:41 (1983)).

It should be noted that only stroma-free hemolysates or washed red blood cells are utilized in the above-cited articles. That is, purification procedures for isolating the hemoglobin component of the stroma-free hemolysates are not described therein. Thus, what is defined as stroma-free hemoglobins therein is in actuality stroma-free hemolysates.

More specifically, about 95% of the hemolysate components is hemoglobin. The remainder consists of proteins and polypeptides whose pharmacological and immunological toxicity is not known. When used for infusion in animals, several grams of hemolysate-containing hemoglobin are injected. Thus, undesirably, hundreds of milligrams of substances of unknown biological activity are also infused into animals when employing a hemolysate.

It should also be noted that in the above-cited references, purification procedures for isolating the desired hemoglobin products from the reaction mixture are not described therein. It is impossible to avoid the presence of overreacted and underacted hemoglobins in the reaction mixtures. These products do not have the desired functional and molecular characteristics.

For the above reasons, it is advantageous to perform chemical treatments on purified hemoglobins, and then to purify the product of the reaction.

Recently, reagents which present a clear advantage over previously employed long chain divalent reagents for producing intramolecular cross-linked hemoglobin have been described (U.S. Pat. No. 5,387,672). These cross-linking reagents give rise to cross-linked hemoglobin which has a lower oxygen affinity, and can be obtained in a much higher yield. While the cross-link is still intramolecular, the hemoglobin thereof has been found to be stable, not only against dissociation, but also against physical agents like heat, pH and aging. Thus, the formation of ferric hemoglobin is greatly retarded with the cross-linked hemoglobin. This allows the use of high temperature heat treatments for eliminating pathogens, the use of lyophilization procedures and to effect storage in liquid form in the cold and at room temperature.

Prevention of dimer dissociation in intramolecularly cross-linked tetramers, prevents glomerular filtration and prolongs the intravascular retention time of the protein (Urbaitis et al, *J. Lab. Clin. Med.,* 117:115 (1991); Bucci et al, *Biomat. Art. Cells & Immob. Biotech.,* 20(2–4):243 (1992); Matheson-Urbaitis et al, *J. Lab. Clin. Med.,* 126:250 (1995); and Ulatowski et al, *Am. J. Phys.,* 270:H466–H475 (1996)). Because nephrotoxicity of filterable (dissociable) hemoglobin results, in part, from intratubular precipitation and hemin formation (Fitzpatrick et al, *Clin. Res.* 42:220 (1994); and Paller, *Am. J. Physiol.,* 255:F539 (1988)), these non-filtered tetramers are expected to be less or non-nephrotoxic.

These stable tetramers of hemoglobins are not filtered at the glomerulus, however this does not rule out their entry into the renal interstitium where other adverse reactions might occur or result after cellular uptake (Urbaitis et al, J. Lab. Clin. Med., 117:115 (1991)). Since these stable hemoglobins have a plasma half time in the rat of about 4 hrs, less than the 6 hrs for albumin, they must have a significant degree of migration into tissues. Post glomerular capillaries are of the fenestrated type with pores having a diameter of 400 to 600 Å, and have a high degree of permeability to small solutes and water. Similar to other capillaries, they function as if they have large and small pores (Rippe et al, *Physiol. Rev.,* 74:163 (1994)). Experimental data indicate that they have a high reflection coefficient for albumin. However, albumin does pass into renal lymph ostensibly through the "large pores". The passage of stable tetrameric hemoglobin into posterior lymph was has been reported (Bleeker et al, *J. Lab. Clin. Med.,* 113:151 (1989)), suggesting that these materials pass over large pores in other capillaries in the body. It has been found that these stable tetramers also appear in renal lymph, even in the complete absence of hemoglobinuria.

The passage of a molecule through the "large pores" is affected by the size of the molecule (Larson et al, *Am. J. Physiol.,* 253:F180 (1987)). Sieving curves generated by relating interstitial concentration to renal venous concentration of inulin, myoglobin, horse radish peroxidase and albumin indicate a retarding effect of molecular size (Aukland et al, *Am. J. Physiol.,* 266:F175 (1994)). The large pore reflection coefficient of albumin with MW 64,000 Da was found to be 0.24 (maximum reflection is 1.0) while that for γ-globulins with MW 156,000–0160,000 Da was 0.44 (Larson et al, *Am. J. Physiol.,* 253:F180 (1987)).

Cross-linked hemoglobin with a similar molecular weight and diameter to albumin would also be expected to pass across "large pores" and enter into the renal interstitium. Based on available data, an increased reflection coefficient would be expected to result as the size of the hemoglobin molecule is increased by polymerization. For example, it would be expected that a polymer of 4 tetrameric Hb units would have a molecular size near 250,000 Da, and would therefore be further retarded in passage across the renal capillaries. Thus, the production of polymerized hemoglobins with a larger molecular diameter (radius) appears to be a rational goal.

Two oxygen carriers, i.e., intramolecularly cross-linked tetramers based on human and bovine hemoglobins, have been extensively characterized and used in physiological trials (Urbaitis et al, *J. Lab. Clin. Med.,* 117:115 (1991); Bucci et al, *Biomat. Art. Cells & Immob. Biotech.,* 20(2–4):243 (1992); Matheson-Urbaitis et al, *J. Lab. Clin. Med.,* 126:250 (1995); and Ulatowski et al, supra). They are stabilized by a covalent cross-link between the β82 lysines of the opposite subunits in the β-cleft of hemoglobin. The linker is either a fumaryl residue (4 carbon long) in bovine hemoglobin or a sebacoyl residue (10 carbon long) in human hemoglobin. The intramolecular cross-link prevents the dissociation of the molecule into dimers and brings the oxygen affinity to a physiologically compatible level. As the molecules do not dissociate into dimers, they are not eliminated in the urine and their intravascular retention time is prolonged to about 4 hrs in the rat and 6 hrs in the cat (Urbaitis et al, *J. Lab. Clin. Med.,* 117:115 (1991); and Ulatowski et al, supra).

These stable tetramers are relatively small and cannot be used at concentrations higher than 6–7%, because of their colloid oncotic pressure (COP) activity per gram. Thus, these infusional fluids have half the oxygen capacity of blood. Therefore, it is very important to develop polymeric hemoglobins which would produce longer retention times, would not migrate into the interstitial fluid and would carry more oxygen per unit of oncotic pressure. The low $COP/O_2$ capacity ratio would allow the production of infusional fluids with very high oxygen capacity, even higher than in normal blood, yet maintaining COP in the usual physiological range.

Polymerized hemoglobins are commonly obtained by treatment with either glutaraldehyde (Sehgal et al, *Transfusion,* 23:158 (1983)), or raffinose (More et al, *Biomat. Art. Cell & Immob. Biotech.,* 20:293 (1992)). With both procedures, the chemical reaction is random and difficult to control. The obtained polymers are highly heterogeneous, with molecular size distributed over a wide range. The starting material is usually natural, dissociable hemoglobin. This adds to the heterogeneity, because polymerization involves both the tetrameric and dimeric forms of hemoglobin. Both kinds of polymers have been used in initial clinical trials without any major side effects (Current Issues in Blood Substitutes Research and Development, San Diego, Calif., March (1995)).

Glutaraldehyde is a bifunctional reagent which produces polymers by forming Schiff bases with the amino groups of lysyl residues in adjacent molecules. The Schiff base is not a stable covalent bond. In its reduced form it is more stable. However, it is not clear whether reducing processes can be used which will reduce 100% of the Schiff bonds. If only a few % of the Schiff bases are not reduced, during metabolic processes in vivo, highly toxic glutaraldehyde can be released.

Polymerization with periodate oxidation and raffinose must be performed in an atmosphere of carbon monoxide and the degraded raffinose linker may still produce a metabolic "indigestion" in vivo.

SUMMARY OF THE INVENTION

Accordingly, an object of the present invention is to provide stable hemoglobin polymers so as to obtain infusional fluids with high oxygen capacity, and long retention times.

An object of the present invention is to use chemical reactions which do not leave chemical linkers in the polymers (defined as zero linkers).

Another object of the present invention is to polymerize molecules of stable non-dissociable tetramers (defined as intramolecularly cross-linked hemoglobin) to reduce the heterogeneity of the product.

Another object of the present invention is to regulate the molecular size of polymerized hemoglobins.

Still another object of the present invention is to provide a cross-linked, polymerized stroma-free hemoglobin having a physiologically acceptable oxygen affinity.

Yet another object of the present invention is to provide a cross-linked, polymerized stroma-free hemoglobin which substantially does not form α-β dimers in vivo.

Still another object of the present invention is to provide a cross-linked, polymerized stroma-free hemoglobin which has a half-life in vivo of at least 6 hr in the rat and 10–12 hr in the cat.

An additional object of the present invention is to provide a cross-linked, polymerized stroma-free hemoglobin having a low viscosity so as to facilitate fluid circulation.

Another object of the present invention is to provide a cross-linked, polymerized stroma-free hemoglobin which is chemically stable for many months.

An additional object of the present invention is to provide a cross-linked, polymerized stroma-free hemoglobin where production can be easily carried out and which can be easily stored and in a stable manner.

Another object of the present invention is to provide a cross-linked, polymerized stroma-free hemoglobin which is devoid of chemical or biological toxicity.

Still another object of the present invention is to provide a reagent for cross-linking hemoglobin so as to simultaneously provide a physiologically acceptable oxygen affinity thereof and prevent the formation of α-β dimers in vivo.

Also, another object of the present invention is to provide a method for cross-linking stroma-free hemoglobin using a reagent which simultaneously provides a physiologically acceptable oxygen affinity thereof and prevents the formation of α-β dimers in vivo.

A still further object of the present invention is to provide a method for cross-linking stroma-free hemoglobin which can be conducted in a single step in the absence of air and oxygen so as to obtain compounds with the desired oxygen affinity.

The above objects of the present invention have been met in one embodiment by stroma-free hemoglobin (Hb) which has been polymerized by formation of intermolecular pseudo-peptide bonds between the surface COOH group(s) on a hemoglobin molecule and the available $NH_2$ group(s) of an adjacent hemoglobin molecule, as shown by the following general formula (I):

$$Hb_m\text{-}(CO\text{—}NH)_n\text{-}Hb_m \quad (I)$$

wherein n is 1 to 48, preferably 1 to 6; and wherein each m is 1 to 1000, preferably 1 to 10; and wherein intermolecular cross-linking is effected by activating, in situ, the surface COOH group(s) of stroma-free hemoglobin, preferably intramolecularly cross-linked stroma-free hemoglobin, (XLHb) with 1-ethyl-3-(3-dimethylaminopropyl)carbodiimide (hereinafter "EDC"), and reacting the activated COOH group(s) with $NH_2$ group(s) of an adjacent hemoglobin molecule(s).

In still another embodiment, the invention provides a method for intermolecularly cross-linking stroma-free hemoglobin with the above-reagent.

BRIEF DESCRIPTION OF THE DRAWINGS

In FIG. 1, "DecHbA" represents stroma-free human hemoglobin intramolecularly crosslinked with a sebacoyl residue.

FIG. 2 shows the two-step reaction of hemoglobin molecules with EDC in the presence of sulfo-NHS. In FIG. 2, as an example, a polymer of only two hemoglobin molecules is shown, as produced by a single intermolecular —CO—NH— bond. "DecHbA", again represents stroma-free human hemoglobin intramolecularly crosslinked with a sebacoyl residue.

In FIG. 3, the numbers refer to the fractions whose analyses are reported in Table 2.

In FIG. 4, the numbers refer to the fractions whose analyses are reported in Table 3.

DETAILED DESCRIPTION OF THE INVENTION

As discussed above, in one embodiment of the present invention, hemoglobin is polymerized by formation of intermolecular pseudo-peptide bonds between the surface COOH group(s) on a hemoglobin molecule and the available $NH_2$ group(s) of an adjacent hemoglobin molecule.

In the present invention, the hemoglobins are polymerized into large molecules (Mw from about 120–20,000 kDa) using "zero-link" technology.

"Zero-link" technology for polymer formation involves the activation, in situ, of the COOH group(s) on the surface of hemoglobin. These activated group(s) are then reacted with the available $NH_2$ group(s) on the surface of an adjacent hemoglobin molecule(s). This forms pseudo-peptide bonds, —CO—HN—, between hemoglobin molecules. There are 58 carboxyl groups and 48 amino groups of the surface of human hemoglobin. Therefore, the formation of several pseudo-peptide bonds results in the formation of large hemoglobin polymers.

Using the "zero-linker" technology, the polymerized hemoglobin of the present invention is represented by the following formula (I):

$$Hb_m\text{-}(CO\text{—}NH)_n\text{-}Hb_m \quad (I)$$

Figure 1:
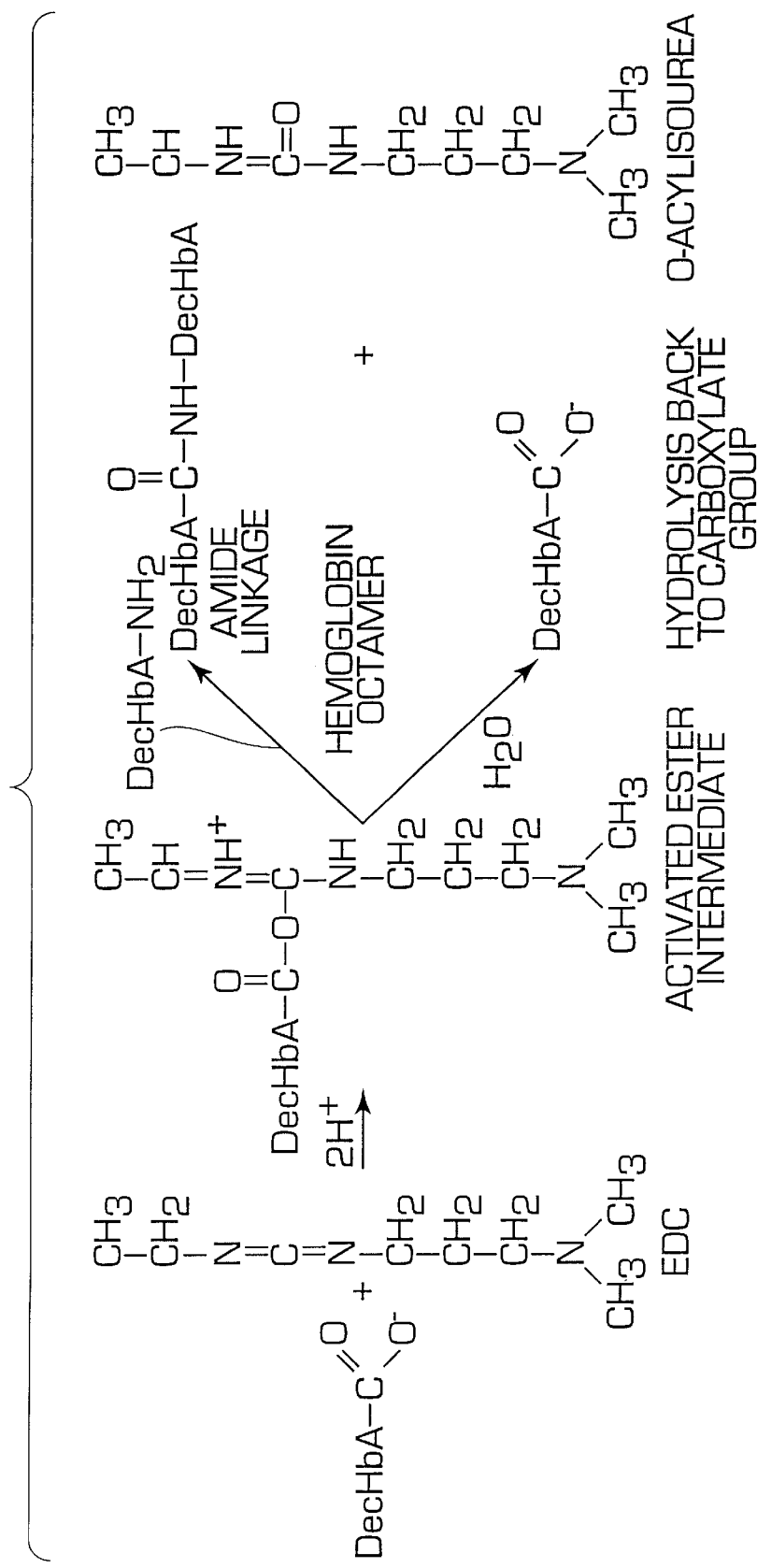
FIG. 1 schematically represents the zero linker polymerization of hemoglobin with EDC.

wherein Hb represents a molecule of hemoglobin, —Co— is one of the surface carboxyl residues, —NH— is an amino group residue on the surface of an adjacent hemoglobin molecule, and n is 1 to 48, preferably 1 to 6; and wherein each m is 1 to 1000, preferably 1 to 10;

The chemistry of the reaction involving polymerization of hemoglobin using EDC (1-ethyl-3-(3-dimethylaminopropyl)carbodiimide) is schematically shown in FIG. 1. The water-soluble carbodiimide EDC activates the side-chain carboxylate groups of the hemoglobin surface (in FIG. 1, DecHbA indicates human hemoglobin intramolecularly cross-linked with a sebacoyl residue), which then reacts with the side-chains of primary amines (the lysyl residues) of another hemoglobin molecule to form a stable amide bond, similar to a peptide bond. The isourea by-product is soluble in aqueous solution and can be easily removed by dialysis. Thus, hemoglobin molecules are polymerized directly by covalent CO—NH bonds between carboxyl and amino groups of adjacent tetramers in the absence of chemical linkers. This reaction can be defined as "zero linker" (Grabarek et al, *Anal. Biochem.*, 185:131 (1990)).

Although the EDC coupling reaction is quite efficient, the activated carboxyl group may be hydrolyzed by water molecules, rather than react with the amino group. A two-step approach to enhance the yield of amide bond formation has been developed (Staros et al, *Anal. Biochem.*, 156:220 (1986)). In this procedure, the addition of N-hydroxysulfosuccinimide (sulfo-NHS) to the carbodiimide reaction results in the formation of an intermediate sulfo-NHS ester, which in turn reacts with amino groups. This reaction is schematically represented in FIG. 2.

The increased stability of the sulfo-NHS ester of the hemoglobin carboxyl groups, compared with that of their corresponding O-acylisourea intermediates, decreases the loss of the activated carboxyl through hydrolysis. Thus, the relative efficiency of the EDC-activated carboxyl group channeled through the nucleophilic attack pathway (formation of amide bond) is increased in the presence of sulfo-NHS. Hence, it is possible to modulate the extent-of polymerization by changing the amounts of sulfo-NHS and EDC in the reaction mixture.

"Zero-link" technology produces polymers in high yields with high solubility and low viscosity. Most importantly, the absence of extramolecular bridges (linkers) avoids the introduction into the infused subject of foreign chemicals which may have toxic effects.

In another embodiment of the present invention, stroma-free hemoglobin is first intramolecularly cross-linked between either the α or the β subunits using active esters of polycarboxylic acids. Intramolecular cross-linking with active polycarboxylic acids is well-known in the art (U.S. Pat. Nos. 4,061,736, 4,598,064, 5,920,919 and 5,387,672). For example, this cross-linking is effected, as disclosed in U.S. Pat. No. 5,387,672, which is incorporated by reference herein in its entirety, using a reagent of general formula (II):

$$R^1OOC\text{---}X^1\text{---}COOR^1 \qquad (II)$$

wherein $R^1$ is a leaving atom or group.

A "leaving atom or group" is well-known in the art and is an electron-rich species which can be an atom or a group of atoms which, by virtue of its capability to stabilize itself by delocalization of its excess negative charge through either resonance effects, inductive effects or charge dissipation, can easily leave, thus making room for an incoming nucleophile. In some instances, the leaving atom or group may contain an electron withdrawing group, which is lost upon the reaction with the nucleophile.

The leaving atom or group represented by $R^1$ can include, among other groups, a halogen atom, a substituted and unsubstituted phosphate ester, and $OR_1$, wherein $R_1$ is selected from the group consisting of a hydrogen atom, a $C_{1-12}$ alkyl group which may be substituted or unsubstituted, a substituted or unsubstituted mono or bicyclic aryl group or a substituted or unsubstituted heterocyclic group. Examples of the substituents on the alkyl, aryl or heterocyclic groups include halogen, CN, $C_{1-12}$ alkyl, phenyl which may be substituted, $NO_2$, OH or $C_{1-12}$ alkoxy, preferably $CH_3$, $C_2H_5$, $C_6H_5$ or $CH_2C_6H_5$.

The $X^1$ group may be a divalent $C_{4-20}$ aliphatic group, which may optionally be intercalated with various groups.

Suitable examples of divalent $C_{4-20}$ aliphatic groups for $X^1$ include $C_{4-20}$ alkyl groups, $C_{4-20}$ alkenyl groups, and $C_{4-20}$ alkynyl groups.

Suitable alkyl groups include substituted and unsubstituted straight chain and branch chain alkyl groups, such as decyl, undecyl, dodecyl, tridecyl and tetradecyl.

Typical examples of alkenyl groups include substituted and unsubstituted straight chain and branch chain alkenyl groups, such as decenyl, undecenyl, dodecenyl, tridecenyl and tetradecenyl.

Appropriate examples of alkynyl groups include substituted and unsubstituted straight and branch chain alkynyl groups, such as decynyl, undecynyl, dodecynyl, tridecynyl and tetradecynyl.

Suitable examples of intercalating moieties for $X^1$ include $C_{1-12}$ alkyl groups, $C_{2-12}$ alkenyl groups, $C_{3-12}$ alkynyl groups, $C_6$ aromatic groups, $C_{5-12}$ alicyclic groups, $C_{5-6}$ heterocyclic groups and fused rings.

Suitable alkyl groups include substituted and unsubstituted straight chain and branch chain alkyl groups, such as propyl, iso-propyl, n-butyl, iso-butyl, tert-butyl, pentyl, hexyl, heptyl, octyl, decyl and dodecyl.

Typical examples of alkenyl groups include substituted and unsubstituted straight chain and branch chain alkenyl groups, such as propenyl, butenyl, butadienyl, pentenyl, hexenyl, heptenyl, octenyl and dodecenyl.

Appropriate examples of alkynyl groups include substituted and unsubstituted straight and branch chain alkynyl groups, such as propynyl and butynyl groups.

Typical examples of aromatic groups include substituted and substituted benzyl and phenyl groups.

Examples of substituted and unsubstituted alicyclic groups include cyclohexyl, cycloheptenyl, cyclooctyl and cyclodecyl groups. These groups may also contain unsaturated bonds as in cyclopentadienyl and cyclohexyldienyl groups.

Other appropriate examples of intercalating moieties for $X^1$ include substituted and unsubstituted $C_{5-6}$ heterocyclic groups including 5- and 6-membered heterocyclic rings containing one or more of oxygen, nitrogen and sulfur atoms as heteroatoms, and examples include pyrrolyl, furanyl, thiophenyl, tetrahydrofuranyl, tetrahydrothiophenyl, pyridinyl and pyrimidinyl groups.

Still other appropriate examples of intercalating moieties for $X^1$ include substituted and unsubstituted fused rings, such as indole, quinoline, benzoquinoline and purine rings.

Each of the above $X^1$ groups may be substituted with one or more substituents such as halogen atoms (e.g., chlorine, bromine and iodine), hydroxy groups, carboxyl groups, sulfato groups, phosphato groups, sulfonyl groups, sulfinyl groups, and the like. Longer chain substituent groups include, for example, polyphosphates, carbohydrates, polyethylene, peptides, fatty acids and lipid moieties.

Each of the above $X^1$ groups can contain one or more chemically reactive groups, besides those producing the cross-link, which may be used for additional chemical reactions either with the same hemoglobin molecule, or with appropriate chemical reagents.

The term "hemoglobin" as used in the present invention means hemoglobin of human, mammal, or any other animal species origin, synthetically produced hemoglobins, hemoglobins obtained by transgenic techniques and in vitro from eukaryotic or prokaryotic cell lines which have been cloned to produce hemoglobin or its subunits, or hemoglobins obtained in mutant form, chemically modified form, or combined form, i.e., a combination of subunits from different species. Examples of hemoglobins include human, marine mammalian, equine, porcine, ovine, bovine, and simian hemoglobin, and additionally fish hemoglobin. Bovine hemoglobin can be obtained, for example, from blood collected from the jugular vein of a cow under sterile conditions into glass bottles containing an acid-citratedextrose (ACD) solution (i.e., containing an anticoagulant) (Fenwal Inc.) to a final 1:8 (v/v). The only requirement is that the hemoglobin employed exhibit high affinity for polyanions, e.g., 2,3-diphosphoglycerate, other polyphosphates, nucleotides and polynucleotides, or other negatively charged mono- or polyvalent anions which regulate hemoglobin's oxygen affinity properties. High affinity for polyanions can be determined as described by Benesch et al, *Biochem.*, 26:162 (1967); and Shimizu et al, *Biochem.*, 13:809 (1974).

The hemoglobin to be treated in the present invention is stroma-free, i.e., substantially free of either cell walls or degradation products of the cell walls, or other phospholipids. Stroma-free red cell hemolysates can be used if desired, although purified hemoglobin is preferred.

The reactivity of hemoglobin with polyanions provides the means by which the reagent of formula (II) of the present invention can be reacted with specific sites on the hemoglobin molecule. In the present invention, the divalent reagent of formula (II) is used to bring, by virtue of its anionic characteristics, amide or enamine bond-forming groups near selected amino groups in the hemoglobin molecule so as to form intramolecular covalent cross-links of the hemoglobin subunits. Although the cross-linking is essentially intramolecular, intermolecular cross-links may also be produced and utilized.

The intramolecular cross-linking bridges inserted into the hemoglobin molecule may also have the electronegativity characteristics necessary for simulating the presence of 2,3-diphosphoglycerate, thereby adjusting the oxygen affinity of stroma-free hemoglobin to physiologically acceptable levels.

The reagents of formulas (I) and (II) of the present invention produce viable products by reacting both with liganded (oxy-, carboxy- or derivatives thereof) and unliganded (deoxy-) hemoglobin. In addition, ferric hemoglobin and its derivatives can also be utilized in the present invention. When the reagents of formula (I) and (II) of the present invention are reacted with deoxy-hemoglobin, the reaction can be performed in the presence of oxygen-absorbing chemicals, for example, sodium dithionite or sodium borohydride, without deleterious effects.

In the present invention, using the reagent of formula (II), only a single chemical treatment is necessary for both adjusting the oxygen affinity and stabilizing the tetrameric structure of hemoglobin. Also, it is not necessary to stabilize newly introduced chemical bonds, using borohydride salts in order to form covalent bonds, as occurs with the known reactions involving aldehydes and polyaldehydes discussed above.

Since the reagent of formula (II) of the present invention is highly specific for selected groups on the hemoglobin molecule, reaction products within limited heterogeneity are obtained. Thus, a high yield of the desired modification product is also obtained. The specificity and necessity of only a single chemical treatment in the present invention simplifies the purification procedures as to the product obtained so that a high yield of essentially uniform molecular species is possible.

The cross-linking of hemoglobin as in the present invention prolongs the retention time of the hemoglobin after transfusion in animals (see Tye et al, *Prog. Clin. Bibl. Res.*, 122:41 (1983); Greenburgh et al, Prog. Clin. Biol. Res., 122:9 (1983); and Urbaitis et al, *J. Lab. Clin. Med.*, 117:115 (1991)). The presence of the cross-links also stabilizes the hemoglobins with respect to physical and chemical agents so as to allow stable and prolonged storage at low cost. Further, the cross-linked hemoglobin of the present invention is very soluble in water and all of the hemes participate in binding and transporting oxygen. Moreover, the viscosity of a 7.0% (w/v) solution of hemoglobin, i.e., a solution of hemoglobin normally used for infusion in humans or animals at 37° C., is less than that of normal blood, and thus such a solution can be advantageously employed.

The cross-linked hemoglobin of the present invention can be infused after solution in standard renal dialysis fluid (e.g., Erilyte 8306, Erika, Inc.) at a concentration of 7.0% (w/v), after filtration through a 0.22 micron filter or some other procedure so as to ensure sterility of the fluids. In mammals, generally 10 to 100% of the circulating blood can be replaced with the cross-linked hemoglobin of the present invention.

Fluids containing the oxygen carriers of the present invention can also be used to prime the pumps necessary to drive surgical equipment, such as that which provides extracorporeal blood circulation. This will save several liters of blood presently used for this purpose. These fluids can be employed in emergency situations for shock therapy, and also have utility in veterinary uses where, in the past, sources of transfusional fluids have been scarce.

In addition, the oxygen carrier is completely soluble in water and can be used in fluids alone or with other oxygen carrier fluids and plasma expanders for transporting oxygen, for example, to isolated perfused organs, to oxygen-consuming environments, or to vital tissues in vivo as components of transfusional agents for medical and veterinary, clinical and surgical practice.

Also, the risks of transmission of infectious diseases (e.g., hepatitis, AIDS, etc.), which can occur with blood transfusions, will be absent using oxygen-carrier fluids containing the cross-linked hemoglobin of the present invention.

A. Preparation of Stroma-Free Hemoglobin

Stroma-free hemoglobin can be prepared, for example, from erythrocytes separated either from freshly drawn blood, from outdated blood, or from pelleted erythrocytes. In order to collect the erythrocytes, the blood samples are washed several times with an isotonic solution, e.g., 5.0 nM phosphate buffer (pH 7.5), and 150 mM NaCl, and the plasma is separated by centrifugation at 3,000 rpm. The washed erythrocytes are then hemolyzed with an equal volume of a hypotonic solution, e.g., 5.0 mM phosphate buffer (pH 7.5). The cellular debris (stroma) still present in the hemolysate is then removed by subsequent filtration, for example, through a 0.5 micrometer Pellicon cassette and a 0.2 micrometer Pellicon cassette (Millipore) or equivalent devices. The filtered hemolysate is referred to as a "stroma-free" hemolysate since it is devoid of particles having diameters larger than 0.2 micrometer. Using a Millipore Pellicon cassette with a nominal 10,000 MW cut-off, the obtained hemolysate is concentrated and equilibrated with desired buffer, e.g., MES, acetate, MOPS, Bis-Tris, Tris or Hepes, preferably 15 mM Tris buffer (pH 8.0).

The hemoglobin is purified from non-hemoproteins, from non-hemoglobinic-hemoproteins and from organic and inorganic contaminants by absorption and subsequent elution on anionic or cationic resins. Examples of suitable anionic resins include DEAE 5PW (Waters) QUE-25/50 (Pharmacia). Examples of suitable cationic resins include 8PC 25/50 (Pharmacia) and SP 5PW (Waters). In the present invention, anionic resins are preferred since they completely remove the organic phosphates that can be bound to the hemoglobin.

Removal of organic phosphates, e.g., 2,3-diphosphoglycerate, is necessary in human hemolysates because the site of choice of the cross-linking reaction employing the reagent of formula (II) in the present invention is the same as that occupied by 2,3-diphosphoglycerate in hemoglobin.

The above-described procedures are generally carried out at a temperature of 4° C. to 10° C. After equilibration with the desired buffer, such as 0.05 M borate buffer (pH 9.1), the purified, stroma-free hemoglobin can be cross-linked, as described in more detail below.

B. Cross-Linking of Stroma-Free Hemoglobin

The reagents of formula (II) the present invention form stable covalent bonds with the amino groups present at the site where hemoglobin binds 2,3-diphosphoglycerate. Other sites of reaction are possible, and acceptable in producing the stabilization of the hemoglobin molecules necessary for physiological oxygen transport. When the reaction with an amino group occurs other than at the 2,3-diphosphoglycerate binding site, intermolecular cross-links can be produced. When the reaction occurs at the 2,3-diphosphoglycerate binding site, which is by far the major reaction, α-β and/or β-β hemoglobin subunit links are formed, which prevent the dissociation of the hemoglobin molecule into the α-β dimers which, as discussed above, are rapidly eliminated in the urine after infusion.

The cross-linking can be performed when hemoglobin either is liganded or unliganded. In order to cross-link the liganded form, the reagents of formula (I) or (II) are added to the purified stroma-free hemoglobin kept under a stream of the necessary gaseous ligands, e.g., oxygen or carbon monoxide, with continuous stirring, at between 4° C. and 10° C. In order to cross-link the unliganded form, the reagents of formula (I) or (II) of the present invention are added to the hemoglobin which is kept in a closed container under nitrogen or some other inert gas at atmospheric pressure. If necessary, residual oxygen is eliminated by the addition of oxygen-absorbing agents, for example, sodium dithionite or borohydride salts in an amount of from 0.5 to 3.0 mg/ml.

The intramolecular cross-linking reaction of the present invention is performed using a molar equivalency or molar excess of the reagent to hemoglobin. Typically, the molar ratio of reagent of formula (II) to hemoglobin is 1:1 to 1:10, preferably 1:2 to 1:6. In addition, typically, the hemoglobin concentration is 3.0% (w/v) to 9.0% (w/v), preferably 6.0% (w/v) in 0.05 borate buffer (pH 9.0). The reaction is allowed to proceed for an appropriate amount of time at the desired temperature, generally for about 1 hr to 3 hr and at 10° C. to 37° C., preferably at 37° C.

The intermolecular cross-linking (polymerizing) reaction of the present invention is typically performed using 5–100 mg/ml of EDC, and optionally 1–20 mg/ml of Sulfo-NHS for about 30–90 min at 37° C. in aerobic or anaerobic conditions. Typically the hemoglobin concentration is 3.0–10 g/dl in 0.1 M 4-morpholino-propane-sulfunate (MOPS).

The reactions of the present invention can be terminated by passing the reaction mixture through a molecular sieving column, e.g., Sephadex column, using pressure (about 1–2 p.s.i.) generated by the same gas employed during the reaction, e.g., oxygen or carbon monoxide using a liganded hemoglobin or nitrogen using an unliganded hemoglobin. This step eliminates any excess reagent used for cross-linking, and can be used for equilibrating the hemoglobin with buffers appropriate for subsequent manipulations.

For the purpose of the present invention, it is preferred to obtain pure and homogeneous products. Thus, the cross-linked hemoglobin is further purified, for example, using chromatography on anionic or cationic resins, in order to eliminate over- or under-reacted hemoglobin resulting from the chemical reaction. Examples of suitable anionic and cationic resins include DEAE 5PW (Waters), SP 5PW (Waters), or QAE-H 25/50 (Spehadex). Gradients made by mixing 15 mM Tris (pH 8.2) and 500 mM Na acetate in 15 mM Tris (pH 7.2) can be used for elution. The purified cross-linked hemoglobin is collected and dialyzed three times with 1:20 (v/v) freshly prepared deionized water, before chromatography.

Exposure to heat can be used to both purify the stabilized tetramers from non-reacted or over-reacted material, and to sterilize the solutions from viruses and other infective agents. This treatment is possible because the presence of the intramolecular cross-link achieved in the present invention confers to hemoglobin a high heat stability, much higher than that of non-cross-linked material.

The incubation mixture is deoxygenated inside a fermentor, or other suitable equipment, by exposure to nitrogen. If necessary, addition of 3–5 mg/ml sodium dithionite removes the last traces of oxygen. Other oxygen absorbers, such as bisulfite, metabisulfite, sulfite and borohydride salts can be employed for this purpose. Additives which prevent formation of aggregates can also be used. These include dithiothreitol, mercaptoethanol, mercaptoacetic acid, and reduced glutathione. This solution is kept at 60–70° C. for 2–10 hr, preferably 2–4 h, then rapidly cooled to 2–5° C. Centrifugation and filtration are used to eliminate the precipitate which is formed, which contain non-cross-linked hemoglobin.

The cross-linked hemoglobin can be stored in water at −80° C. Storage at higher temperatures, between −80° and 4° C. can be carried out upon addition of dextran 70 (e.g., 6.0% (w/v)) in 0.9% (w/v) NaCl and/or reducing agents, like ascorbic acid (e.g., 3.0 mg/ml) together with a chelating agent, such as EDTA (e.g., 0.01–0.1 mg/ml) or vitamin E (e.g., 0.5 mg/ml) In this manner, the cross-linked hemoglobin is stable for weeks, at the very least, to several months.

C. Analyses for Polymer Characteristics

The presence of intermolecular cross-links can be assessed, e.g., by gel filtration (see Ackers, *Adv. Protein Chem.*, 24:343 (1972)), ultracentrifuge analysis (see Schachman, *Biochem.*, 2:884 (1963)), or by light scattering (see Schmitz, *Dynamic Light Scattering by Macromolecules*, Academic Press, New York, N.Y. (1990)).

When using ultracentrifuge analysis, the presence of polymers in the hemoglobin solution can be ascertained by measuring the sedimentation velocity of the hemoglobin. The sedimentation constants, $S_{20,w}$, for tetramers is 4.4. Higher values are obtained for polymeric forms (see Schachman, supra).

The extent of polymerization can also be assessed using SDS urea-gel electrophoresis (see Swank et al, *Anal. Biochem.*, 39:462 (1971)). In this method, the hemoglobin is unfolded with SDS and disulfide bridges are broken so that the velocity of electrophoretic migration inside of the matrix of the supporting gel is determined only by the size, i.e., the molecular weight of its monomeric subunits. In the absence of the intramolecular cross-linking modifications, hemoglobin in SDS electrophoresis produces one band corresponding to a molecular weight of 16,000 Daltons, as is expected from the size of its monomeric subunits. On the other hand, if it is intramolecularly cross-linked, bands corresponding to polymeric units of higher molecular weight are obtained.

The ability of hemoglobin to reversibly bind oxygen is dependent upon the ferrous state, i.e., oxidation state, of the iron of the heme. Thus, to maximize reversible oxygen binding capability, the process of the present invention and purification steps should be conducted under conditions that do not produce irreversible oxidation of the iron atom to its ferric form. Analyses of the absorption spectra of hemoglobin in the visible region can be employed in order to estimate the amount of ferric hemoglobin present in the final product (see Benesch et al, *Anal. Biochem.*, 11:81 (1965)).

D. Determination of Oxygen Affinity

Oxygen affinity of cross-linked hemoglobin can be measured using the Hemoxyanalyzer (trade name for an oxygen dissociation analyzer produced by TCS, Huntington Valley, Pa.) or the Gill cell described in Dolman et al, *Anal. Biochem.*, 87:127 (1978).

These measurements are preferably performed at 37° C. in 0.15 M Tris buffer (pH 7.4) and 0.15 M NaCl, so as to mimic physiological conditions in vivo. Oxygen absorption by hemoglobin is characterized by two parameters. One is the value of "P½" i.e., the partial pressure of oxygen sufficient for saturating 50% of the hemoglobin present in solution. The other is the value of "n" in the Hill equation (see Wyman, *Adv. Prot. Chem.,* 19:23 (1964)) which at best simulates the oxygen binding curves and which is the expression of the oxygen binding cooperativity of the hemoglobin in solution. In vivo in humans, both parameters affect the amount of oxygen transported by hemoglobin from the lungs to the tissues. Inside red blood cells, human hemoglobin has values of P½=27 mmHg and n near 3.0. Using the Hill equation and assuming that the partial pressure of oxygen in the lungs is 100 mmHg, and that at the tissue it is 30 mmHg (see Bard, *Medical Physiology* (Mosby, C. V. (1956)), these characteristics assure a delivery to the tissues of 40% of the oxygen absorbed in the lungs by hemoglobin. The same is expected from a cell-free oxygen carrier with the same characteristics. The delivery of 25% of the oxygen bound by hemoglobin is generally considered sufficient to support life in humans in a resting state. This is the transport produced by an oxygen carrier with P½=18 mmHg and n=1.3. For this reason, acceptable hemoglobin-based oxygen carriers are those with P½=18 mmHg or higher, and n=1.3 or higher. This procedure can also be used, with modifications as necessary, to determine physiological competence in species other than humans.

E. Measurement of Retention Times In Vivo of Cross-linked Hemoglobin (Intravascular Persistence)

Rabbits and rats are preferentially used for measurement of retention times in vivo of the cross-linked hemoglobin of the present invention because of their small size. After sedation and anesthetization, as necessary for maintaining the animals in a pain-free state, catheters are inserted into one carotid artery and one jugular vein. Blood is withdrawn from the artery while the liquid containing the cross-linked hemoglobin is infused through the vein, in an amount representing 40% of the blood volume. The plasma concentration of the cross-linked hemoglobin can then be measured in samples of blood withdrawn from the animal immediately after the infusion, 30 min later, and then hourly for 12 hr.

Preferentially, activation of the carboxyl groups in formula (II) will be through esterification with 3,5-dibromosalicyl. Other forms of activation are possible. The esters of 3,5-dibromosalicyl are known to have high specificity for the β82 and α99 lysines of human hemoglobin (see Klotz et al, *J. Biol. Chem.,* 260:16215 (1985); and Chatterjee et al, *J. Biol. Chem.,* 261:9929 (1986)). The use of reagents without this specificity is inconvenient because of the large numbers of unwanted compounds which are formed during the reaction with hemoglobin Esterification with 3,5-dibromosalicyl can be achieved as described by Razynska et al, *J. Chem. Soc. Perkin Trans.,* 2:1531–1540 (1991).

The following examples are further provided for illustrative purposes only and are in no way intended to limit the scope of the present invention.

SYNTHESIS EXAMPLES

A. Synthesis of bis(3,5-dibromosalicyl)-sebacate(DecBDA)

Sebacoyl-dichloride (Aldrich) (0.01 mol) in dry tetrahydrofuran (THF) (10 ml) was added dropwise to two equivalents of tert-butyl 3,5-dibromosalicylate (see Delaney et al, Arch. Biochem. Biophys., 228:627 (1984)), which had previously been treated with a stoichiometric amount of NaH in THF. The mixture was stirred for 5 hr at room temperature, and the solvent was then removed under reduced pressure. The residue was dissolved in diethyl ether and extracted several times with water. The extract was dried over $MgSO_4$, filtered and concentrated. Recrystallization from ethanol gave a pure product, as shown by thin layer chromatography. The resulting product (2.0 mmol) was dissolved in anhydrous trifluoroacetic acid (10 ml), and allowed to stand at room temperature. After 30 min, the solvent was removed under reduced pressure and the precipitate recrystallized from trifluoroacetic acid or ethyl alcohol (see Razynska et al, supra).

B. Synthesis of bis(3,5-dibromosalicyl)adipate (AdipBDA)

Adipoyl dichloride (Aldrich) (0.01 mol) in dry tetrahydrofuran (THF) (10 ml) was added dropwise to two equivalents of tert-butyl 3,5-dibromosalicylate (see Delaney et al, supra), which had previously been treated with a stoichiometric amount of NaH in THF. The mixture was stirred for 5 hr at room temperature, and the solvent was then removed under reduced pressure. The residue was dissolved in diethyl ether and extracted several times with water. The extract was dried over $MgSO_4$, filtered and concentrated. Recrystallization from ethanol gave a pure product, as shown by thin layer chromatography. The resulting product (2.0 mmol) was dissolved in anhydrous trifluoroacetic acid (10 ml), and allowed to stand at room temperature. After 30 min, the solvent was removed under reduced pressure and the precipitate recrystallized from trifluoroacetic acid or ethyl alcohol (see Razynska et al, supra).

EXAMPLE 1

Preparation of Stroma-Free Hemoglobin

One unit of outdated human blood obtained from a blood bank was poured into centrifuge containers and spun at 4° C., 3,000 rpm for 20 min to remove the plasma fraction. The pelleted erythrocytes were suspended and washed with 10 volumes of isotonic buffer (5.0 mM phosphate (pH 7.5) and 150 mM NaCl) and centrifuged at 4° C., 3,000 rpm for 20 min. The supernatant was removed by aspiration. This procedure was repeated three times.

Alternatively, bovine blood was collected in an ACD solution from the jugular vein of a cow of the Hereford breed, and the red cells were collected and washed in the same manner as described above for human blood. All of the procedures described below were applied to the resulting human and bovine blood.

The pelleted erythrocytes were then hemolyzed by addition of hypotonic buffer (5.0 mM phosphate (pH 7.5)), to a final volume of 8.0 liters and filtered first through a 0.5 micrometer Millipore Pellicon cassette, then through a 0.2 micrometer Millipore Pellicon cassette, in order to separate the stroma from the stroma-free hemoglobin solution that filtered through the cassette. The stroma-free hemoglobin solution was concentrated, using a low molecular weight cut-off Millipore Pellicon cassette, with a cut-off at 10,000 MW, to a final volume producing a 10% (w/v) solution. The concentrated hemoglobin solution was then dialyzed using the same Pellicon cassette against 40 liters of 20 mM Tris buffer (pH 8.0).

Alternatively, the hemolyzate was delipidated by emulsification with $CHCl_3$ in a ratio 10:1 (v/v), and stirred in the cold for at least 1–2 hr. The emulsion was resolved by centrifugation at 10,000 rpm for 30 min, and the hemoglobin in the supernatant used for further treatments.

In order to purify the hemoglobin component from the stroma-free hemolysate thus obtained, 1.0 g of the stroma-free hemoglobin was absorbed on an anionic resin (DEAE PW5, (Waters)) and chromatographed using a gradient formed by 15 mM Tris (pH 8.0) and 15 mM Tris (pH 8.0), and 500 nM NaCl. A Waters (Milford, MA) Delta-Prep 4000 high-performance liquid chromatography (HPLC) machine was employed for the chromatography. The major peak corresponding to pure hemoglobin was collected. The various minor fractions eluted before and after the major peak were discarded. The pure stroma-free hemoglobin was dialyzed 3 times against 1:20 (v/v) of freshly prepared deionized-distilled water and stored at −80° C.

EXAMPLE 2

Preparation of Intramolecularly Cross-Linked Hemoglobin Using DecBDA or AdipBDA and Oxy-hemoglobin Human oxy-hemoglobin, at a concentration of 60 mg/ml in 0.05 M Tris buffer (pH 7.2) was equilibrated at 37° C., before adding 2.0 mg/ml of DecBDA reagent. In addition, bovine oxy-hemoglobin, at a concentration of 60 mg/ml in 0.05 M Tris buffer (pH 7.2) was equilibrated at 37° C., before adding 2.0 mg/ml of AdipBDA reagent. The incubations continued with gentle stirring for 2 hr at 37° C. and were stopped with the addition of 13 mg/ml of glycyl-glycine, for 30 min at 37° C. During this period of time, the solutions were kept under oxygen at atmospheric pressure in a closed container. The incubation mixtures were dialyzed overnight against a cold 1.0 g/l glycine buffer (pH 7.6) previously equilibrated with oxygen at atmospheric pressure, then they were equilibrated with the buffers used for the chromatographic analyses as described in Example 4.

EXAMPLE 3

Preparation of Intramolecularly Cross-linked Hemoglobin Using DecBDA or AdipBDA and Deoxy-hemoglobin Human or bovine oxy-hemoglobin, at a concentration of 60 mg/ml, in 0.05 M borate buffer (pH 8.5) was equilibrated at 37° C. while flushing the system with nitrogen in order to remove oxygen. After flushing for 30 min, 0.5 mg/ml of dithionite dissolved in 0.05 M borate buffer (pH 7.6) were added to the solution to remove the last traces of oxygen. As a result, the hemoglobin was completely deoxygenated. Then, 3.0 mg/ml of DecBDA reagent (using human hemoglobin) or AdipBDA reagent (using bovine hemoglobin) were added to the solution. The incubation continued with gentle stirring for 90 min at 37° C., and was stopped with the addition of 13 mg/ml of glycyl-glycine, for 15 min at 37° C. During this period of time, the solution was continuously flushed with nitrogen previously humidified by passage through a washing bottle containing deoxygenated water. The incubation mixture was dialyzed for 1 hr against cold 1.0 g/l glycine previously equilibrated with nitrogen, so as to remove the dissolved oxygen, then overnight against cold 1.0 g/l glycine buffer (pH 7.6) previously equilibrated with oxygen at atmospheric pressure. Then, the mixture was equilibrated with the buffers used for the chromatographic analyses as described in Example 4.

EXAMPLE 4

Purification of Intramolecularly Cross-Linked Hemoglobins

As discussed above, it is preferred that the cross-linked hemoglobins of the present invention are obtained as a pure homogeneous component containing a single molecular species. Thus, a final purification step was conducted by chromatography on a DEAE PW5 column using an Altek HPLC machine or a preparative Waters Delta-prep 4000 HPLC equipment.

More specifically, the cross-linked hemoglobins of Examples 2 and 3 above, were equilibrated with 15 mM Tris (pH 8.0), absorbed on the DEAE PW5 column and eluted using a gradient formed by 15 mM Tris (pH 8.0) and 15 mM Tris (pH 8.0) and 500 mM NaCl (pH 8.0). Three peaks were obtained, wherein the first was residual untreated hemoglobin, the second, which was the major fraction, represented cross-linked hemoglobin, and the third represented a small component of overreacted hemoglobin. If necessary, the chromatography is repeated on the eluted material until a complete separation is obtained of the various fractions.

The purity of the samples was assessed by microzone electrophoresis. The pure cross-linked hemoglobin produced single sharp bands, with different mobility than untreated hemoglobin.

In SDS-urea electrophoresis (see Swank et al, supra) the purified fractions gave two bands corresponding to molecular weights of 32,000 and 16,000 Daltons, respectively. Optical scanning of the gel using a Joyce and Loeble microdensitometer indicated a relative proportion of 1:1 between the two bands, as expected from the cross-linking of only one pair of like subunits per molecule of tetrameric hemoglobin.

Sedimentation velocity experiments on the cross-linked hemoglobin gave sedimentation constants near $S_{20,w}=4.4$, both in 0.05 M phosphate buffer, (pH 7.0), and in 0.05 M Bis-Tris buffer (pH 5.5). This value of the sedimentation constant is characteristic of tetrameric, non-dissociated hemoglobin. This demonstrates the inability of these cross-linked hemoglobins to dissociate into diners; normal hemoglobin in 0.05 M Bis-Tris buffer acquires a sedimentation velocity near $S_{20,w}=3.5$, because it dissociates into dimers.

EXAMPLE 5

Determination of Oxygen Affinities of Various Cross-Linked Purified Hemoglobins

The cross-linked hemoglobins purified as described in Example 4, were equilibrated with 0.15 M Tris-HCl (pH 7.4), and their oxygen affinities were measured with a Hemoscan at 37° C. The results obtained are shown in the following Table 1:

TABLE 1

Oxygen Affinity of Hemoglobin Treated with DecBDA or AdipBDA

| Sample | P½ (mmHg) | n | % Delivery to Tissues of the Oxygen Bound by Hemoglobin in the Lungs |
|---|---|---|---|
| Human blood | 27 | 2.8 | 40 |
| Human hemoglobin (untreated) | 18 | 2.6 | 20 |
| Human oxy-hemoglobin (DecHbA)) | 18 | 1.3 | 24 |
| Human deoxy-hemoglobin (DecHbA) | 34 | 2.2 | 47 |
| Bovine blood | 31 | 2.7 | 48 |
| Bovine hemoglobin (untreated) | 31 | 2.7 | 48 |

TABLE 1-continued

Oxygen Affinity of Hemoglobin Treated with DecBDA or AdipBDA

| Sample | P½ (mmHg) | n | % Delivery to Tissues of the Oxygen Bound by Hemoglobin in the Lungs |
|---|---|---|---|
| Bovine oxy-hemoglobin (AdipHbBv) | 22 | 1.8 | 30 |
| Bovine deoxy-hemoglobin (AdipHbBv) | 53 | 2.3 | 59 |

Note:
The last column in Table 1 shows values computed with the Hill equation (Wyman, Adv. Prot. Chem., 19:223 (1964)), assuming that the partial pressure of oxygen is 100 mmHg in the lungs and 30 mmHg in the tissues. DecBDA = bis(3,5-dibromosalicyl) sebacate. AdipBDA = bis(3,5-dibrosalicyl) adipate.

In Table 1 above, P½ indicates the partial pressure of oxygen necessary for saturating hemoglobin at the 50% level (i.e., P½ measures the oxygen affinity). Also, the value n is the expression of oxygen-binding cooperativity, which in normal human red cells is very close to n=3.

As shown in Table 1 above, the oxy-reacted cross-linked stroma-free hemoglobin obtained as described above had an oxygen affinity lower than that of the corresponding untreated stroma-free hemoglobin. In addition, all of the cross-linked stroma-free human hemoglobins obtained had a value of n in the Hill plot of at least 1.3, demonstrating the persistence of a good oxygen-binding cooperativity in the cross-linked hemoglobins.

Also as shown in Table 1 above, the oxygen-binding characteristics of all of the cross-linked hemoglobins assured acceptable levels of oxygen delivery to tissues.

EXAMPLE 6

Polymerization of Hemoglobin Using EDC (Zero Linker)

A. Zero Linker Polymerization of DecHbA (i.e., Human Hemoglobin Intramolecularly Cross-linked with a Sebacoyl Residue) (PolyA)

Figure 3A:
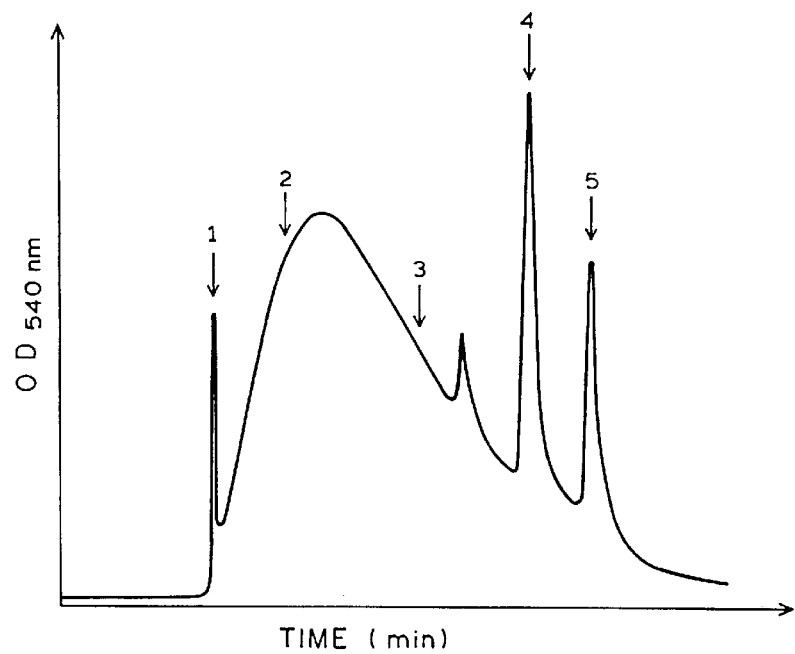
FIGS. 3A and 3B show the results of anion-exchange chromatography of polymerized Deoxy-DecHbA (FIG. 3A); and Oxy-DecHbA (FIG. 3B) using a DEAE-MCI resin.

6.0% (w/v) of oxy-DecHbA, obtained as described in Example 2 above, was polymerized in the presence of 10 mg/ml EDC and 2.0 mg/ml sulfo-NHS in 0.1 M MES (pH 6.7) at room temperature for 3 hrs. The reaction was stopped by the addition of glycyl-glycine to a final concentration of 0.1 M, followed by dialysis against 0.1 M glycine (pH 8.0). The resulting solution was dialyzed against 0.015 M Tris/acetate (pH 8.2). Then, the mixture of polymers was chromatographed on a DEAE-MCI matrix (Mitsubishi Kasei Co., Tokyo, Japan) using a gradient of 0.015 M Tris/acetate (pH 8.2), and 0.015 M Tris/acetate in 0.5 M sodium acetate (pH 7.2). The elution profile of the chromatography is shown in FIG. 3A. The marked fractions were collected and tested for P½ and the average radius. The average molecular radius of the molecules in solution was estimated using dynamic light scattering (DynaPro-801 Molecular Size Detector, marketed by Protein Solutions, Charlottesville, Va). The scattering data are biased in favor of the largest molecules in solution. The data are reported in Table 2 below.

Figure 3B:
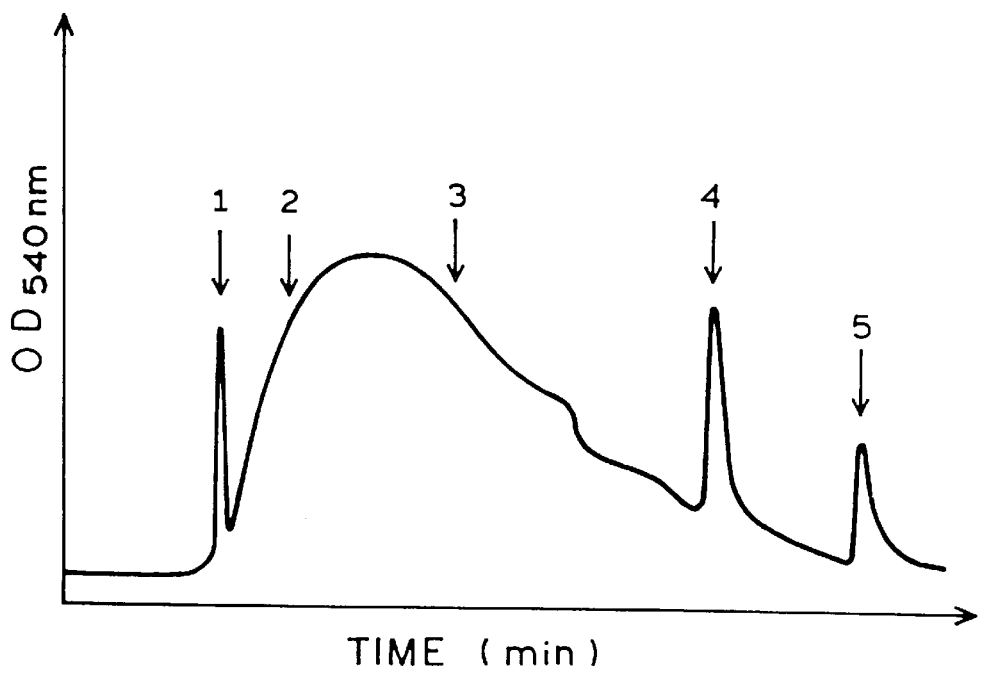

Deoxy-DecHbA, obtained as described in Example 3 above, was polymerized with EDC in the same manner, but under anaerobic conditions. Chromatography of the polymers mixture was carried out under the same conditions as for Oxy-DecHbA. The elution profile is presented in FIG. 3B. The P½ and average molecular radius of the marked fractions are reported in Table 2 below.

All of the obtained polymers were readily soluble in water. The data in FIGS. 3A and 3B clearly indicate the presence of several distinct populations of polymers. In both kinds of polymers, obtained under aerobic and anaerobic conditions, fraction 1 probably still contains non-polymerized DecHbA, fractions 2 and 3 suggest the presence of polymers centered at 3-mer and 8-mer of DecHbA, respectively. Fractions 4 and 5 include highly polymerized species. The sharp chromatographic resolution of the highly polymerized fractions and of the non-polymerized ones underscore the usefulness of ionic exchange chromatography for reducing the heterogeneity of polymerized DecHbA.

TABLE 2

| Chromatography Fraction | P½ (mmHg) | Radius (nm) | Nominal Molecular Weight (kDa) |
|---|---|---|---|
| DecHbA | 34 | 3.2 | 64 |
| DEOXY | | | |
| crude mixture | 16.7 | 6.1 | 443 |
| 1 | 20.5 | 3.8 | 107 |
| 2 | 20.5 | 4.5 | 178 |
| 3 | 19.5 | 6.6 | 561 |
| 4 | 18.3 | 9 | 1423 |
| 5 | 12.9 | 10.2 | 2072 |
| OXY | | | |
| crude mixture | 11.7 | 5.5 | 324 |
| 1 | 12.4 | 3.7 | 99 |
| 2 | 9.8 | 4.2 | 144 |
| 3 | 10.9 | 5.2 | 274 |
| 4 | 11.3 | 7.6 | 857 |
| 5 | 11.4 | 10.5 | 2260 |

In Table 2 above, the average molecular weights were estimated from the respective radii, assuming that the polymers still have a spherical shape. NMW=$(radius/3.2)^3 \times 64,000$. The radius of DecHbA is 3.2 nm, which is as expected for tetrameric hemoglobin with a MW of 64,000 Da. The value of n in the Hill plots was between 1.3 and 1.7 in all of the preparations.

B. Zero Linker Polymerization of AdipHbBv (i.e., Bovine Hemoglobin Intramolecularly Cross-linked with an Adipoyl Residue) (PolyB)

Figure 4A:
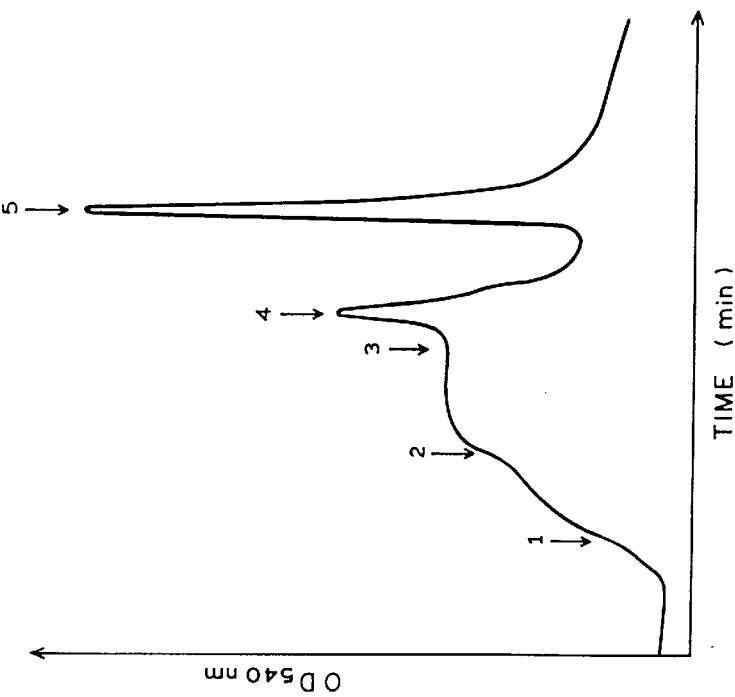
FIGS. 4A and 4B show the results of anion-exchange chromatography of polymerized Deoxy-ADIPHbBv (FIG. 4A); and Oxy-ADIPHbBv (FIG. 4B) using DEAE-MCI resin.

6.0% (w/v) oxy-AdipHbBv, obtained as described in Example 2, above was polymerized in the presence of 10 mg/ml EDC and 2.0 mg/ml sulfo-NHS in 0.1 M MES (pH 6.7) at 37° C. for 90 min. The reaction was stopped by the addition of glycyl-glycine to a final concentration of 0.1 M, followed by dialysis against 0.1 M glycine (pH 8.0). The resulting solution was dialyzed against 0.015 M Tris/acetate (pH 8.2). The mixture of polymers was chromatographed on a DEAE-MCI matrix using a gradient of 0.015 M Tris/acetate (pH 8.2), and 0.015 M Tris/acetate in 0.5 M sodium acetate (pH 7.2). The elution profile of the chromatography is shown in FIG. 4A. The P½ and the average radius were measured for marked fractions. These data are presented in Table 3 below.

Figure 4B:
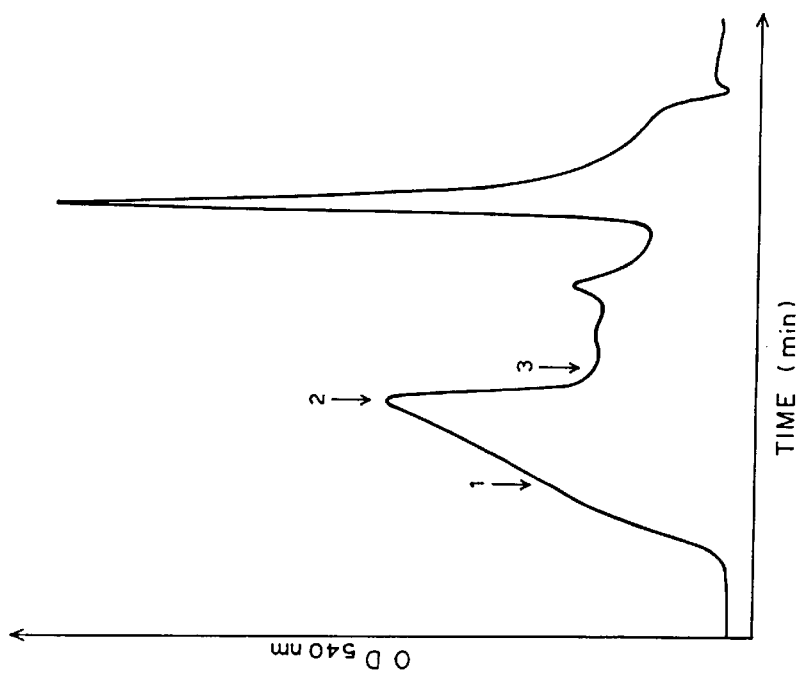

Deoxy-AdipHbBv obtained as described in Example 3 above, was polymerized in the same manner, only under anaerobic conditions. The chromatographic profile is shown in FIG. 4B. P½ and molecular radius of collected fractions are reported in Table 3 below.

Also in this case, ionic exchange chromatography very efficiently recognized the molecular size of the polymers. Table 3 below clearly shows that AdipHbBv polymerizes more readily than DecHbA, especially in its deoxy-form. It also produces polymers with physiologically competent oxygen affinity even for highly polymerized material. The low affinity of the polymers obtained under anaerobic conditions is unprecedented. During the manipulations of these chromatographic fractions, even those with highly polymerized material like fractions 4 and 5, the viscosity of the solutions did not appear to be higher than that of normal unpolymerized hemoglobin.

TABLE 3

| Chromatography Fraction | P½ (mmHg) | Radius (nm) | Nominal Molecular Weight (kDa) |
|---|---|---|---|
| AdipHbBv | 53.1 | 3.2 | 64 |
| DEOXY | | | |
| crude mixture | 33.2 | 14.4 | 5832 |
| 1 | 51.9 | 4.7 | 203 |
| 2 | 46.5 | 5.2 | 274 |
| 3 | 42.3 | 9.1 | 1471 |
| 4 | N/A | 13.4 | 4699 |
| 5 | N/A | 30.6 | 55962 |
| OXY | | | |
| crude mixture | 19.5 | 15.5 | 7273 |
| 1 | 19.4 | 6.1 | 443 |
| 2 | 20.1 | 7.0 | 669 |
| 3 | 20.1 | 9.5 | 1674 |

In Table 3 above, the average molecular weights were estimated from the respective radii, assuming that the polymers still have a spherical shape. NMW=(radius/3.2 )$^3 \times$64,000. The radius of AdipHbBv is 3.2, as expected for tetrameric hemoglobin with a MW of 64,000 Da. The value of n in the Hill plots was between 1.3 and 1.7 in all of the preparations.

EXAMPLE 7

Plasma Retention and Urinary Excretion in Rats and in Cats

Experiments on rats and cats were performed to determine whether the animals would tolerate the polymerized hemoglobin of the present invention without discomfort, other than that due to the necessary surgery, and to measure the half-time of retention in circulation of the infused polymerized hemoglobin. The two polymers obtained in Example 6, under anaerobic conditions, were used in these experiments, namely PolyA (i.e., zero-link polymerized DecHbA, fraction 3–5 in Table 2) and PolyB (i.e., zero-link polymerized AdipHbBv, fraction 2–4 in Table 3).

Plasma retention and urinary excretion were determined in anesthetized rats (male Sprague Dawley rats weighing between 300–350 g, which were anesthetized, i.p., with 120 mg of Inactin per kg); and in anesthetized cats (mixed breed female cats weighing 2.5–3.5 kg, which were anesthetized, i.p., with a 40 mg bolus of pentobarbital sodium per kg, and i.v., with 6.0 mg of pentobarbital sodium per kg per hr infusion).

Catheters were inserted into the right femoral artery for assessment of blood pressure, right femoral vein for delivery of hydrating solutions or of the polymeric hemoglobin solutions, and left femoral artery to allow for withdrawal of blood.

In the rats, either PolyA or PolyB were administered by a 50% exchange transfusion with a 6.0% (w/v) solution of the chosen polymeric hemoglobin. The bladder was catherized to obtain timed urine samples. The exchange was accomplished at a rate of 0.8 ml/min. Urine and 0.2 ml blood samples were collected at 20 min time intervals post-exchange for at least 2 hrs.

In the cats, the protocol was the same, except that only PolyA was used, and mechanical ventilation was performed after oral endotracheal intubation so as to maintain the arterial partial pressure of carbon dioxide between 35–45 mmHg. Inspired oxygen was 25–30% so as to maintain arterial partial pressure of oxygen greater than 100 mmHg. Arterial pH was maintained between 7.35–7.45 with i.v. administration of 1.0 mEq/ml sodium bicarbonate. Lactate-Ringer's solution was infused at a rate of 4.0 ml/kg/hr. Exchange transfusion of 30 ml of a 7.0 g/dl solution (2.1 g) of polyA was performed over a 10 min period. Blood samples (0.8 ml) were drawn at 20 to 30 min intervals, and urine was collected at 20 min intervals for a period of 7 hrs.

In both animal groups, urine and plasma samples were analyzed for hemoglobin concentration by measuring the absorbance of the CO formed at 420 nm in samples appropriately diluted with a phosphate buffer (pH 7.0), and saturated with Co. A few grains of sodium dithionite were added to the samples in order to reduce ferric forms of hemoglobin to ferrous carbonmonoxy hemoglobin. Plasma half-time and volume of distribution were determined using linear polynomial regression procedures.

The results for the rat experiments are shown in Table 4 below.

TABLE 4

| Hb | con % | COP mmHg | R nm | P½ mmHg | n | v rel to H$_2$O | Na | K | ml/100 | plasma mg/ml | U | HT h | MAP PRE | MAP POST |
|---|---|---|---|---|---|---|---|---|---|---|---|---|---|---|
| PolyA | 8.0 | 26 | 12.1 | 20.2 | 1.4 | 1.6459 | 134 | 3.4 | 1.5 | 28 | t | 8.0 | 123 | 152 |
| PolyA | 7.0 | 23 | 12.3 | 20.1 | 1.4 | 1.5156 | 131 | 3.4 | 1.6 | 28 | t | 9.9 | 146 | 141 |
| PolyA | 6.0 | 16 | 14.1 | 19.8 | 1.3 | 1.4202 | 136 | 2.5 | 1.6 | 28 | t | 8.2 | 133 | 136 |
| PolyB | 7.0 | 15 | 12.5 | 44.2 | 1.4 | 1.5119 | 131 | 2.9 | 1.3 | 18 | t | 7.0 | 140 | 147 |

PolyA = polymer of human hemoglobin (DecHbA)
PolyB = polymer of bovine hemoglobin (AdipHbBv)
Con % = concentration of polymers in the infusion fluid
COP = colloid osmotic pressure (normal in the rat near 20 mmHg)
R nm = average radius of polymer in nanometer
P½ = oxygen affinity (blood P½ = 27–30 mmHg)
n = cooperativity index (blood n = 3)
v rel to H$_2$O = relative viscosity with respect to the viscosity of water
Na = sodium content of infusing fluid
K = potassium content in the infusion fluid
ml/100 g = milliliters of fluid injected per 100 g of rat
plasma mg/ml = concentration of polymer in plasma at the end of infusion
U = urine elimination, t = traces
HT h = half time of retention in hours
MAP PRE = mean arterial pressure before infusion
MAP POST = mean arterial pressure at the end of infusion In the cat, there was a transient MAP increase from 125 mmHg (PRE) to 160 mmHg (POST). All of the data in the cat corresponded very well with that in Table 4 above for the rat experiments.

All of the animals survived the experiments, in the sense that the rat had to be sacrificed at the end of about 4 hrs of observation, and the cat after about 8 hrs of observation.

The half-time of retention was 7–8 hrs in the rats and 13 hrs in the cat. Both the rat and the cat showed the presence in the urine of a very light hemoglobinuria, which disappeared in the later samples. The total amount of polymers eliminated in the urine has been estimated to less than 1.0% of the total infused material. The infused material contained less than 5.0% of ferric hemoglobin.

While the invention has been described in detail and with reference to specific embodiments thereof, it will be apparent to one skilled in the art that various changes and modifications can be made therein without departing from the spirit and scope thereof.

What is claimed is:

1. Stroma-free polymerized hemoglobin intermolecularly cross-linked represented by the following general formula (I)

$$Hb_m\text{-}(CO\text{---}NH)_n\text{-}Hb_m \qquad (I)$$

wherein Hb represents a molecule of stroma-free hemoglobin, —CO— is one of its surface carboxyl residues, —HN— is an amino group residue on the surface of an adjacent hemoglobin molecule, and n is 1 to 48; and wherein each m is 1 to 1000.

2. The stroma-free polymerized hemoglobin as claimed in claim 1, wherein n is 1 to 6; and each m is 1 to 10.

3. The stroma-free polymerized hemoglobin as claimed in claim 1, wherein said hemoglobin is also intramolecularly cross-linked.

4. The stroma-free polymerized hemoglobin as claimed in claim 3, wherein said hemoglobin is intramolecularly cross-linked with a compound of the following formula (II):

$$R^1OOC\text{---}X^1\text{---}COOR^1 \qquad (II)$$

wherein $R^1$ is a leaving atom or group capable of activating the carboxyl moiety to which it is attached and $X^1$ is a divalent hydrocarbon.

5. The stroma-free polymerized hemoglobin as claimed in claim 4, wherein $X^1$ is a divalent $C_{4\text{-}20}$ aliphatic group, which may optionally be intercalated with at least one member selected from the group consisting of a $C_{1\text{-}12}$ alkyl group, a $C_{2\text{-}12}$ alkenyl group, a $C_{3\text{-}12}$ alkynyl groups, a $C_6$ aromatic group, a $C_{5\text{-}12}$ alicyclic group, a $C_{5\text{-}6}$ heterocyclic group and a fused ring.

6. The stroma-free polymerized hemoglobin as claimed in claim 5, wherein said divalent $C_{4\text{-}20}$ aliphatic group is selected from the group consisting of a $C_{4\text{-}20}$ alkyl group, a $C_{4\text{-}20}$ alkenyl group, and a $C_{4\text{-}20}$ alkynyl group.

7. The stroma-free polymerized hemoglobin as claimed in claim 6, wherein said $C_{4\text{-}20}$ alkyl group is selected from the group consisting of decyl, undecyl, dodecyl, tridecyl and tetradecyl.

8. The stroma-free polymerized hemoglobin as claimed in claim 6, wherein said $C_{4\text{-}20}$ alkenyl group is selected from the group consisting of decenyl, undecenyl, dodecenyl, tridecenyl and tetradecenyl.

9. The stroma-free polymerized hemoglobin as claimed in claim 6, wherein said $C_{4\text{-}20}$ alkynyl group is selected from the group consisting of decynyl, undecynyl, dodecynyl, tridecynyl and tetradecynyl.

10. The stroma-free polymerized hemoglobin as claimed in claim 5, wherein said $C_{1\text{-}12}$ alkyl group is selected from the group consisting of propyl, iso-propyl, n-butyl, iso-butyl, tert-butyl, pentyl, hexyl, heptyl, octyl, decyl and dodecyl.

11. The stroma-free polymerized hemoglobin as claimed in claim 5, wherein said $C_{2\text{-}12}$ alkenyl group is selected from the group consisting of propenyl, butenyl, butadienyl, pentenyl, hexenyl, heptenyl, octenyl and dodecenyl.

12. The stroma-free polymerized hemoglobin as claimed in claim 5, wherein said $C_{3\text{-}12}$ alkynyl group is selected from the group consisting of propynyl and butynyl.

13. The stroma-free polymerized hemoglobin as claimed in claim 5, wherein said $C_6$ aromatic group is selected from the group consisting of benzyl and phenyl.

14. The stroma-free polymerized hemoglobin as claimed in claim 5, wherein said $C_{5\text{-}12}$ alicyclic group is selected from the group consisting of cyclohexyl, cycloheptenyl, cyclooctyl and cyclodecyl.

15. The stroma-free polymerized hemoglobin as claimed in claim 5, wherein said $C_{5\text{-}6}$ heterocyclic group is selected from the group consisting of pyrrolyl, furanyl, thiophenyl, tetrahydrofuranyl, tetrahydrothiophenyl, pyridinyl and pyrimidinyl.

16. The stroma-free polymerized hemoglobin as claimed in claim 5, wherein said fused ring is selected from the group consisting of indole, quinoline, benzoquinoline and purine.

17. The stroma-free polymerized hemoglobin as claimed in claim 4, wherein $R^1$ is selected from the group consisting of a hydrogen atom, a substituted or unsubstituted phosphate ester, and $OR_1$, wherein $R_1$ is selected from the group consisting of a hydrogen atom, a $C_{1\text{-}12}$ alkyl group which may be substituted or unsubstituted, a substituted or unsubstituted mono or bicyclic aryl group or a substituted or unsubstituted heterocyclic group.

18. The stroma-free polymerized hemoglobin as claimed in claim 1, wherein said stroma-free hemoglobin is selected from the group consisting of human, equine, porcine, ovine, bovine, simian and fish hemoglobin.

19. The stroma-free polymerized hemoglobin as claimed in claim 18, wherein said stroma-free hemoglobin is bovine hemoglobin.

20. The stroma-free polymerized hemoglobin as claimed in claim 18, wherein said stroma-free hemoglobin is human hemoglobin.

21. The stroma-free polymerized hemoglobin as claimed in claim 1, wherein said cross-linking is carried out in the presence of oxygen.

22. The stroma-free polymerized hemoglobin as claimed in claim 1, wherein said cross-linking is carried in the absence of oxygen.

23. A method for producing stroma-free polymerized hemoglobin intermolecularly cross-linked hemoglobin of the following formula(I):

$$Hb_m\text{-}(CO\text{---}NH)_n\text{-}Hb_m \qquad (I)$$

wherein Hb represents a molecule of stroma-free hemoglobin, —CO— is one of its surface carboxyl residues, —HN— is an amino group residue on the surface of an adjacent hemoglobin molecule; n is 1 to 48; and wherein each m is 1 to 1000; comprising the steps of:

(A) activating, in situ, COOH group(s) of stroma-free hemoglobin with 1-ethyl-3-(3-dimethylaminopropyl) carbodiimide, and (B) reacting the activated COOH group(s) with $NH_2$ group(s) of an adjacent hemoglobin molecule(s).

24. The method as claimed in claim 23, wherein n is 1 to 6; and each m is 1 to 10.

25. The method as claimed in claim 23 wherein step (A) is carried out in the presence of N-hydroxysulfosuccinimide.

26. The method as claimed in claim 23 wherein said hemoglobin is also intramolecularly cross-linked.

27. The method as claimed in claim 26, wherein prior to step (A), said hemoglobin is intramolecularly with a compound of the following formula (II):

$$R^1OOC-X^1-COOR^1 \qquad (II)$$

wherein $R^1$ is a leaving atom or group capable of activating the carboxyl moiety to which it is attached and $X^1$ is a divalent hydrocarbon.

28. The method as claimed in claim 27, wherein $X^1$ is a divalent $C_{4-20}$ aliphatic group, which may optionally be intercalated with at least one member selected from the group consisting of a $C_{1-12}$ alkyl group, a $C_{2-12}$ alkenyl group, a $C_{3-12}$ alkynyl groups, a $C_6$ aromatic group, a $C_{5-12}$ alicyclic group, a $C_{5-6}$ heterocyclic group and a fused ring.

29. The method as claimed in claim 28, wherein said divalent $C_{4-20}$ aliphatic group is selected from the group consisting of a $C_{4-20}$ alkyl group, a $C_{4-20}$ alkenyl group, and a $C_{4-20}$ alkynyl group.

30. The method as claimed in claim 29, wherein said $C_{4-20}$ alkyl group is selected from the group consisting of decyl, undecyl, dodecyl, tridecyl and tetradecyl.

31. The method as claimed in claim 29, wherein said $C_{4-20}$ alkenyl group is selected from the group consisting of decenyl, undecenyl, dodecenyl, tridecenyl and tetradecenyl.

32. The method as claimed in claim 29, wherein said $C_{4-20}$ alkynyl group is selected from the group consisting of decynyl, undecynyl, dodecynyl, tridecynyl and tetradecynyl.

33. The method as claimed in claim 28, wherein said $C_{1-12}$ alkyl group is selected from the group consisting of propyl, iso-propyl, n-butyl, iso-butyl, tert-butyl, pentyl, hexyl, heptyl, octyl, decyl and dodecyl.

34. The method as claimed in claim 28, wherein said $C_{2-12}$ alkenyl group is selected from the group consisting of propenyl, butenyl, butadienyl, pentenyl, hexenyl, heptenyl, octenyl and dodecenyl.

35. The method as claimed in claim 28, wherein said $C_{3-12}$ alkynyl group is selected from the group consisting of propynyl and butynyl.

36. The method as claimed in claim 28, wherein said $C_6$ aromatic group is selected from the group consisting of benzyl and phenyl.

37. The method as claimed in claim 28, wherein said $C_{5-12}$ alicyclic group is selected from the group consisting of cyclohexyl, cycloheptenyl, cyclooctyl and cyclodecyl.

38. The method as claimed in claim 28, wherein said $C_{5-6}$ heterocyclic group is selected from the group consisting of pyrrolyl, furanyl, thiophenyl, tetrahydrofuranyl, tetrahydrothiophenyl, pyridinyl and pyrimidinyl.

39. The method as claimed in claim 28, wherein said fused ring is selected from the group consisting of indole, quinoline, benzoquinoline and purine.

40. The method as claimed in claim 28, wherein $R^1$ is selected from the group consisting of a hydrogen atom, a substituted or unsubstituted phosphate ester, and $OR_1$, wherein $R_1$ is selected from the group consisting of a hydrogen atom, a $C_{1-12}$ alkyl group which may be substituted or unsubstituted, a substituted or unsubstituted mono or bicyclic aryl group or a substituted or unsubstituted heterocyclic group.

41. The method as claimed in claim 23, wherein said stroma-free hemoglobin is selected from the group consisting of human, equine, porcine, ovine, bovine, simian and fish hemoglobin.

42. The method as claimed in claim 41, wherein said stroma-free hemoglobin is bovine hemoglobin.

43. The method as claimed in claim 41, wherein said stroma-free hemoglobin is human hemoglobin.

44. The method as claimed in claim 23, wherein said cross-linking is carried in the presence of oxygen.

45. The method as claimed in claim 23, wherein said cross-linking is carried in the absence of oxygen.

* * * * *

UNITED STATES PATENT AND TRADEMARK OFFICE
CERTIFICATE OF CORRECTION

| | | |
|---|---|---|
| PATENT NO. | : 5,998,361 | Page 1 of 1 |
| APPLICATION NO. | : 08/733413 | |
| DATED | : December 7, 1999 | |
| INVENTOR(S) | : Enrico Bucci and Anna Tazynska | |

It is certified that error appears in the above-identified patent and that said Letters Patent is hereby corrected as shown below:

Delete Column 1, lines 3-5 and replace with --This invention was made with government support under grant numbers RO1-HL13164 and PO1-HL-48517, awarded by the National Institutes of Health. The government has certain rights in the invention--.

Signed and Sealed this

Nineteenth Day of February, 2008

JON W. DUDAS
*Director of the United States Patent and Trademark Office*